United States Patent
Faler et al.

(10) Patent No.: US 11,746,163 B2
(45) Date of Patent: Sep. 5, 2023

(54) ISOHEXANE-SOLUBLE UNSATURATED ALKYL ANILINIUM TETRAKIS(PERFLUOROARYL)BORATE ACTIVATORS

(71) Applicant: ExxonMobil Chemical Patents Inc., Baytown, TX (US)

(72) Inventors: Catherine A. Faler, Houston, TX (US); Margaret T. Whalley, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 326 days.

(21) Appl. No.: 17/141,874

(22) Filed: Jan. 5, 2021

(65) Prior Publication Data

US 2022/0220229 A1    Jul. 14, 2022

(51) Int. Cl.

| | |
|---|---|
| *C07F 5/02* | (2006.01) |
| *C07C 211/63* | (2006.01) |
| *C07C 211/64* | (2006.01) |
| *C08F 4/643* | (2006.01) |
| *C08F 4/52* | (2006.01) |
| *C08F 110/06* | (2006.01) |
| *C08F 210/16* | (2006.01) |
| *C08F 4/659* | (2006.01) |

(52) U.S. Cl.
CPC ............. *C08F 4/52* (2013.01); *C07C 211/64* (2013.01); *C07F 5/02* (2013.01); *C07F 5/027* (2013.01); *C08F 4/65908* (2013.01); *C08F 110/06* (2013.01); *C08F 210/16* (2013.01)

(58) Field of Classification Search
CPC ...... C07F 5/02; C08F 4/65908; C07C 211/63; C07C 211/64
See application file for complete search history.

(56) References Cited

U.S. PATENT DOCUMENTS

| | | | |
|---|---|---|---|
| 5,919,983 A | 7/1999 | Rosen et al. | 568/3 |
| 6,121,185 A | 9/2000 | Rosen et al. | 502/164 |
| 7,087,602 B2 | 8/2006 | Thomas et al. | 514/234.5 |
| 7,101,940 B2 | 9/2006 | Schottek et al. | 526/134 |
| 7,799,879 B2 | 9/2010 | Crowther et al. | 526/134 |
| 7,985,816 B2 | 7/2011 | Crowther et al. | 526/160 |
| 8,580,902 B2 | 11/2013 | Crowther et al. | 526/160 |
| 8,642,497 B2 | 2/2014 | Berris | 502/202 |
| 8,835,587 B2 | 9/2014 | Crowther et al. | 526/348 |
| 2002/0062011 A1 | 5/2002 | Campbell et al. | 534/15 |
| 2015/0203602 A1 | 7/2015 | Sun et al. | C08F 4/52 |
| 2019/0330392 A1 | 10/2019 | Faler et al. | C08F 10/02 |

FOREIGN PATENT DOCUMENTS

| | | | |
|---|---|---|---|
| WO | 2002/002577 | 1/2002 | ............ C07F 17/00 |
| WO | 2019/210026 | 10/2019 | ............ C07F 5/02 |

*Primary Examiner* — Caixia Lu

(57) ABSTRACT

The present disclosure describes highly soluble activators for use in olefin polymerization processes. These activators are ionic ammonium borates and have the general formula $[Ar(ER^1R^2H)(R^3)][tetrakis(perfluoroaryl)borate]$ where Ar is an aromatic group; E is nitrogen or phosphorous; $R^1$ is independently selected from aliphatic hydrocarbyl groups containing 1 to 30 carbon atoms, preferentially methyl; $R^2$ and $R^3$ are independently selected from aliphatic hydrocarbyl groups containing 10 to 30 carbon atoms and at least one internal olefin. The inventive activators dissolve in isohexane or methylcyclohexane at 25° C. to form homogeneous solutions of at least 10 mM concentration. When combined with a group 4 metallocene to form an active olefin polymerization catalyst, the inventive activators are shown to have activity similar to controls.

11 Claims, 3 Drawing Sheets

ISOHEXANE-SOLUBLE UNSATURATED ALKYL ANILINIUM TETRAKIS(PERFLUOROARYL)BORATE ACTIVATORS

FIELD

The present disclosure relates to activators for use in a polymerization process, and more particularly to ionic ammonium borate activators.

BACKGROUND

Polyolefins are widely used commercially because of their robust physical properties. Polyolefins are typically prepared with a catalyst that polymerizes olefin monomers. Therefore, there is interest in finding new catalysts and catalyst systems that provide polymers having improved properties.

Aliphatic hydrocarbon soluble activators are useful because they remove the need for aromatic solvents in olefin polymerization processes. A soluble anilinium borate (ACT1-BF28) is known.

PCT Patent Publication WO/US2019/210026 describes a soluble anilinium borate activator.

U.S. Pat. No. 5,919,983 discloses polymerization of ethylene and octene using a catalyst system comprising $[(C_{18})_2MeN)]^+[B(PhF_5)_4]^-$ activator having four fluoro-phenyl groups bound to the boron atom and two linear $C_{18}$ groups bound to the nitrogen, as well as describing other linear groups at column 3, line 51 et seq.

U.S. Pat. No. 8,642,497 discloses the preparation of N,N-dimethylanilinium tetrakis(heptafluoronaphth-2-yl)borate anion.

US 2003/0013913 (granted as U.S. Pat. No. 7,101,940) discloses various activators such as N,N-dimethylcyclohexylammoniumtetrakis(pentafluorophenyl)borate [0070], and N,N-diethylbenzylammoniumtetrakis(pentafluorophenyl)borate [0124].

US 2002/0062011 discloses phenyl dioctadecylammonium(hydroxyphenyl) tris(pentafluorophenyl) borate at paragraph [0200] and (pentafluorophenyl) dioctadecylammonium tetrakis(pentafluorophenyl) borate at paragraph [0209].

U.S. Pat. Nos. 7,799,879, 7,985,816, 8,580,902, 8,835,587, and WO 2010/014344 describe ammonium borate activators that include some that use a tetrakis(heptafluoronaphth-2-yl)borate anion.

There is a need for activators that are soluble in aliphatic hydrocarbons and capable of producing polyolefins having a high molecular weight and high melt temperature. Likewise, there is a need for activators that are soluble in aliphatic hydrocarbons and capable of producing polyolefins at high activity levels where the polymers preferably have high molecular weight and/or high melt temperature.

Other references of interest include: WO 2002/002577; U.S. Pat. Nos. 7,087,602; 6,121,185; 8,642,497; US 2015/0203602; and US 2019/0330392.

SUMMARY

A compound represented by Formula (AI): $[Ar(ER^1R^2H)(R^3)]^+[BR^4R^5R^6R^7]^-$ (AI) wherein, Ar is an aromatic group, E is nitrogen or phosphorous, $R^1$ is independently selected from aliphatic hydrocarbyl groups containing 1 to 30 carbon atoms, each of $R^2$ and $R^3$ is independently selected from aliphatic hydrocarbyl groups containing 10 to 30 carbon atoms and at least one internal olefin, and each of $R^4$, $R^5$, $R^6$, and $R^7$ is independently substituted phenyl or substituted naphthyl, wherein at least one of $R^4$, $R^5$, $R^6$, and $R^7$ is substituted with from one to seven fluorine atoms.

The compound where $R^1$ is methyl.

The compound where E is phosphorous.

The compound where E is nitrogen.

The compound where each of $R^4$, $R^5$, $R^6$, and $R^7$ is independently substituted phenyl.

The compound where each of $R^4$, $R^5$, $R^6$, and $R^7$ is independently substituted naphthyl.

The compound where the olefin is hanging off of $R^3$.

The compound further comprising a catalyst compound, wherein the catalyst compound and the compound represented by Formula (AI) form a catalyst system.

The compound where the catalyst compound includes a group 4 metallocene.

A method, comprising: introducing one or more monomers, an activator, and catalyst system into a reactor under polymerization conditions; and obtaining a polymer, wherein the activator is a compound represented by Formula (AI): $[Ar(ER^1R^2H)(R^3)][BR^4R^5R^6R^7]$ (AI) wherein, Ar is an aromatic group, E is nitrogen or phosphorous, $R^1$ is independently selected from aliphatic hydrocarbyl groups containing 1 to 30 carbon atoms, each of $R^2$ and $R^3$ is independently selected from aliphatic hydrocarbyl groups containing 10 to 30 carbon atoms and at least one internal olefin, and each of $R^4$, $R^5$, $R^6$, and $R^7$ is independently substituted phenyl or substituted naphthyl, wherein at least one of $R^4$, $R^5$, $R^6$, and $R^7$ is substituted with from one to seven fluorine atoms.

The method where the polymer includes an ethylene copolymer.

The method where the ethylene copolymer includes an ethylene-octene copolymer.

The method where the polymer includes propylene.

DETAILED DESCRIPTION

Definitions

Figure 1:
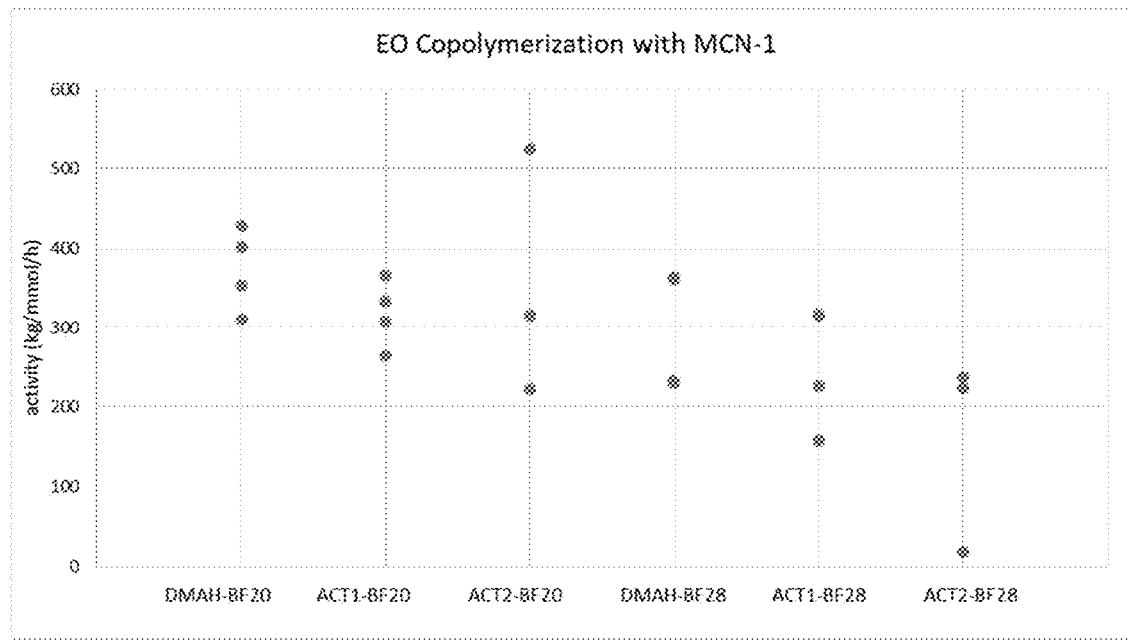
FIG. 1 is a graph illustrating activity using activators embodying the present technological advancement in an ethelyne-octene (EO) copolymerization process.

Unless otherwise noted all melt temperatures (Tm) are DSC second melt and are determined using the following DSC procedure according to ASTM D3418-03. Differential scanning calorimetric (DSC) data are obtained using a TA Instruments model Q200 machine. Samples weighing about 5 to about 10 mg are sealed in an aluminum hermetic sample pan. The DSC data are recorded by first gradually heating the sample to about 200° C. at a rate of about 10° C./minute. The sample is kept at about 200° C. for about 2 minutes, then cooled to about −90° C. at a rate of about 10° C./minute, followed by an isothermal for about 2 minutes and heating to about 200° C. at about 10° C./minute. Both the first and second cycle thermal events are recorded. The melting points reported herein are obtained during the second heating/cooling cycle unless otherwise noted.

All molecular weights are weight average (Mw) unless otherwise noted. All molecular weights are reported in g/mol unless otherwise noted. Melt index (MI) also referred to as I2, reported in g/10 min, is determined according to ASTM D-1238, 190° C., 2.16 kg load. High load melt index (HLMI) also referred to as I21, reported in g/10 min, is determined according to ASTM D-1238, 190° C., 21.6 kg load. Melt index ratio (MIR) is MI divided by HLMI as determined by ASTM D1238.

For the purposes of the present disclosure, the numbering scheme for the Periodic Table Groups is the "New" notation as described in *Chemical and Engineering News*, v. 63(5), pg. 27 (1985).

For purposes of the present disclosure, a "catalyst system" is a combination of at least one catalyst compound, an activator, and an optional support material. The catalyst systems may further comprise one or more additional catalyst compounds. For the purposes of the present disclosure, when catalyst systems are described as comprising neutral stable forms of the components, it is well understood by one of ordinary skill in the art, that the ionic form of the component is the form that reacts with the monomers to produce polymers. Activators represented by Formula (AI) are intended to embrace ionic forms in addition to the neutral forms of the compounds.

In the description herein, a catalyst may be described as a catalyst precursor, a pre-catalyst compound, a catalyst compound or a transition metal compound, and these terms are used interchangeably. A polymerization catalyst system is a catalyst system that can polymerize monomers into polymer.

"Catalyst activity" is a measure of the level of activity of the catalyst and is reported as the mass of product polymer (P) produced per mole (or mmol) of catalyst (cat) used (kgP/molcat or gP/mmolCat), and catalyst activity can also be expressed per unit of time, for example, per hour (hr), e.g., (Kg/mmol h).

The terms "cocatalyst" and "activator" are used herein interchangeably and are defined to be any compound which can activate a catalyst compound by converting the neutral catalyst compound to a catalytically active catalyst compound cation.

For purposes herein an "olefin," alternatively referred to as "alkene," is a linear, branched, or cyclic compound comprising carbon and hydrogen having at least one double bond.

For purposes herein a "polymer" has two or more of the same or different monomer ("mer") units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, copolymer, as used herein, can include terpolymers and the like. An oligomer is typically a polymer having a low molecular weight, such as Mn of less than 25,000 g/mol, or less than 2,500 g/mol, or a low number of mer units, such as 75 mer units or less or 50 mer units or less. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn.

Exemplary Embodiments

The exemplary activator embodiments described herein are ionic ammonium borates and have the general Formula (AI):

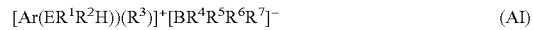

$$[Ar(ER^1R^2H)(R^3)]^+[BR^4R^5R^6R^7]^- \quad (AI)$$

wherein,

Ar is an aromatic group,

E is nitrogen or phosphorous, $R^1$ is independently selected from aliphatic hydrocarbyl groups containing 1 to 30 carbon atoms, preferably methyl, each of $R^2$ and $R^3$ is independently selected from aliphatic hydrocarbyl groups containing 10 to 30 carbon atoms and at least one internal olefin, and each of $R^4$, $R^5$, $R^6$, and $R^7$ is independently substituted phenyl or substituted naphthyl, wherein at least one of $R^4$, $R^5$, $R^6$, and $R^7$ is substituted with from one to seven fluorine atoms.

The aromatic group for Ar can be any aromatic ring or rings. For example, Ar could benzene, naphthalene, cyclcopentadiene, anthracene, or any other ring structure that follows the Huckel rule.

$R^1$ can also be ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like. $R^1$ can also have a number of carbon atoms for any other range of values between 1 to 30.

$R^2$ and $R^3$ can each independently be heptadecyl or octadecane. $R^2$ and $R^3$ can each independently also have a number of carbon atoms for any other range of values between 10 to 30. $R^2$ and $R^3$ can both have an internal olefin, but both do not need to have an internal olefin.

The borates can be tetrakis(heptafluoronapth-2-yl)borate or tetrakis(pentafluorophenyl)borate.

An anilinium activator embodying the present technological advancement includes a double bond, wherein in the present embodiment the olefin in $R^3$ has the double bond. Conventional thinking is that a double bond could interfere with polymerization. However, in this exemplary embodiment, the double bond is internal (not at the end of a chain), and the data herein evidences good polymerization relative to controls.

The activators of Formula (AI) dissolve in isohexane or methylcyclohexane at 25° C. to form homogeneous solutions of at least 10 mM concentration. When combined with a group 4 metallocene to form an active olefin polymerization catalyst, the activators embodying the present technological advancement are shown to have activity similar to controls (data provided below).

Using the previously established synthesis for ACT1, the olefinic intermediate was converted into an HCl salt then the subsequent borate salts. It should be noted that this synthesis was attempted previously and failed due to high temperature required to exchange the chloride with a borate. However, a recent synthetic improvement (discussed in patent publication WO 2019/0210029) enables this exchange at ambient or room temperature (any reference to room temperature in this application is at about 23° C.).

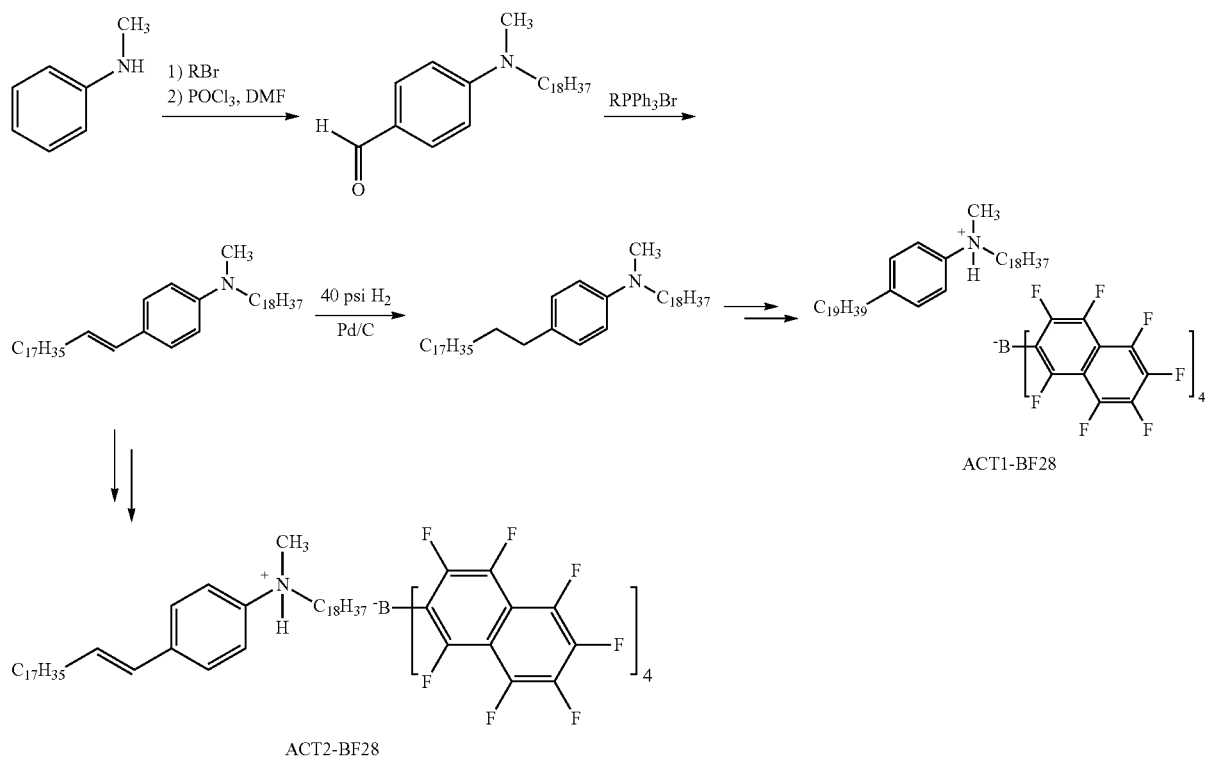

N,N-Dimethylanilinium tetrakis(pentafluorophenyl)borate (DMAH-BF20) was purchased from Albemarle. Sodium tetrakis(heptafluoronaphthalen-2-yl)borate (Na-BF28) and N,N-dimethylanilinium tetrakis(heptafluoronaphthalen-2-yl)borate (DMAH-BF28) were purchased from Grace Davison. Lithium tetrakis(pentafluorophenyl)borate etherate (Li-BF20) was purchased from Boulder Scientific. All other reagents and solvents were purchased from Sigma-Aldrich. NMR spectra were recorded on a Bruker 500 or 400 NMR with chemical shifts referenced to residual solvent peaks (CDCl3: 7.27 ppm for 1H, 77.23 ppm for 13C).

The general synthesis of ammonium borate activators is described below.

Ammonium borate activators were prepared using a two-step process. In the first step, an amine is dissolved in a solvent (e.g. hexane, cyclohexane, methylcyclohexane, ether, dichloromethane, toluene) and an excess (ca. 1.2 molar equivalents) of hydrogen chloride is added to form an ammonium chloride salt. This salt is typically isolated by filtration from the reaction medium and dried under reduced pressure. The isolated ammonium chloride is then heated to reflux with one molar equivalent of an alkali metal borate in a solvent (e.g. cyclohexane, dichloromethane, methylcyclohexane) to form the ammonium borate along with byproduct alkali metal chloride, the latter which typically is removed by filtration. Examples describing the synthetic details for selected ammonium borates are given below.

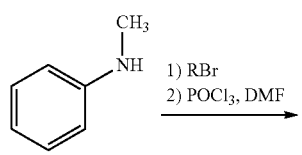

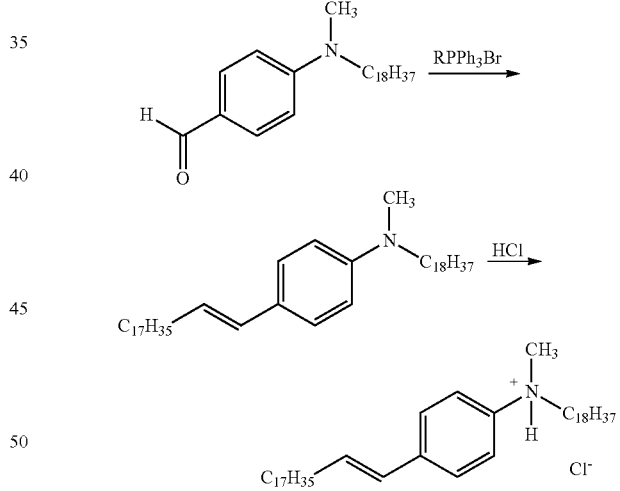

N-methyl-N-octadecylaniline: N-methylaniline (10.2 g, 96 mmol), bromoctadecane (38.4 g, 115 mmol), and triethylamine (19.9 mL, 144 mmol) were dissolved in 400 mL of DMSO and heated overnight at 100° C. The solution was diluted with water and extracted three times with ethyl acetate. The organic fractions were combined, rinsed with brine, dried with MgSO4 and concentrated to yield a yellow oily solid. The product was purified by silica gel chromatography (2% ethyl acetate/isohexane) and isolated as a white solid. $^1$H NMR (400 MHz, CDCl$_3$, δ): 0.88 (t, J=8.0 Hz, 3H), 1.25 (m, 32H), 1.56 (m, 2H), 2.92 (s, 3H), 3.29 (m, 2H), 6.68 (m, 3H), 7.22 (m, 2H).

4-(methyl(nonadec-1-enyl)amino)benzaldehyde: To DMF (0.34 mL, 4.4 mmol) cooled to 0° C., was added phosphoryl chloride (0.49 mL, 5.3 mmol) dropwise. The reaction was warmed to room temperature over 30 minutes, turning bright red. It was cooled to 0° C. and a solution of the above alkylated was aniline (1.6 g, 4.4 mmol) in 20 mL of THF added. After stirring for 20 minutes, the reaction was heated at 80° C. for 2 hours. The cooled solution was quenched by dropwise addition of 20 mL of 1M KOH. The mixture was extracted with three portions of 15 mL EtOAc. The organic fractions were combined, rinsed with brine, dried with MgSO4, and concentrated. The orange residue was purified by silica gel chromatography (2% ethyl acetate/isohexane) and isolated as a pale pink crystalline solid in 70% yield. $^1$H NMR (400 MHz, CDCl$_3$, δ): 0.88 (t, J=7.0 Hz, 3H), 1.25 (m, 30H), 1.61 (m, 2H), 3.04 (s, 3H), 3.39 (t, J=8.0 Hz, 2H), 6.69 (d, J=7.0 Hz, 2H), 7.72 (d, J=7.0 Hz, 2H), 9.72 (s, 1H).

N-Methyl-4-(nonadec-1-enyl)-N-octadecylaniline: The above aldehyde (100 g, 258 mmol) and octadecyltriphenylphosphonium bromide (184.3 g, 310 mmol) were preheated to 55-60° C. in anhydrous THF (1.8 L). Potassium tert-butoxide (31.8 g, 284 mmol) was added portion wise over 5 minutes. The reaction was refluxed for 2 hours. Additional potassium tert-butoxide (2 g, 18 mmol) was added and the reaction was refluxed for 10 minutes. After cooling to room temperature, the solvent was removed under reduced pressure. The residue was triturated with ethyl acetate (1 L) and water (1 L), the insoluble white product was filtered off and washed with ethyl acetate (3×100 mL) to give the title compound (160 g, 99% yield, 95% purity) as a 9 to 1 mixture of E and Z isomers. This mixture (160 g) was dissolved in ethyl acetate (1 L) and heated at 55-60° C. for 30 minutes, then filtered hot. This trituration and hot filtration was repeated to give just the E-isomer (102 g) as a white solid. The filtrate was left overnight, then filtered to give a 4 to 1 mixture of E and Z isomers (46.5 g, 92% combined yield) as a white solid.

N-methyl-4-(nonadec-1-enyl)-N-octadecylanilinium chloride: The above aniline (1.50 g, 2.40 mmol) was dissolved in 100 mL of hexane. Ethereal HCl (1.44 mL, 2M) was added and a white precipitate formed within 10 minutes. The reaction was stirred 45 minutes before collecting the solid salt (89% yield).

N-methyl-4-(nonadec-1-enyl)-N-octadecylanilinium tetrakis(heptafluoronaphthalen-2-yl)borate: The above anilinium chloride salt (0.066 g, 0.10 mmol) was slurried with Na-BF28 (0.105 g, 0.10 mmol) in 20 mL of dichloromethane at ambient temperature for 1.5 hours. When cooled to ambient, the solution was filtered and concentrated to a brown oil. The borate salt was obtained in 83% yield:

$^1$H NMR (500 MHz, CDCl$_3$, δ): 0.87 (m, 6H), 1.25 (m, 58H), 1.49 (m, 4H), 2.25 (m, 2H), 3.26 (s, 3H), 3.47 (t, J=8.0 Hz, 2H), 6.30 (m, 2H), 7.10 (d, J=8.2 Hz, 2H), 7.31 (d, J=8.5 Hz, 2H).

N-methyl-4-(nonadec-1-enyl)-N-octadecylanilinium tetrakis(pentafluorophenyl)borate: The above anilinium chloride salt (0.44 g, 0.67 mmol) was slurried with Li-BF20 (0.51 g, 0.67 mmol) in 20 mL of isohexane at ambient temperature for 2 hours. The solution was filtered and concentrated to a green solid. The borate salt was obtained in 70% yield: $^1$H NMR (400 MHz, CDCl$_3$, δ): 0.87 (m, 6H), 1.25 (m, 60H), 1.47 (m, 2H), 2.29 (m, 2H), 3.28 (br s, 3H), 3.50 (m, 2H), 5.89 (dt, J=11.5, 7.3 Hz, 1H), 6.40 (d, J=11.8 Hz, 1H), 7.22 (m, 2H), 7.48 (m, 2H).

Examples of polymerization in a parallel pressure reactor are described below.

Skeletal diagrams of conventional activators (DMAH-BF20, DMAH-BF28, ACT1-BF20, and ACT1-BF28), conventional catalyst compounds (MCN-1 and MCN-2), and activators embodying the present technological advancement (ACT2-BF-20 and ACT2-BF-28) are shown below.

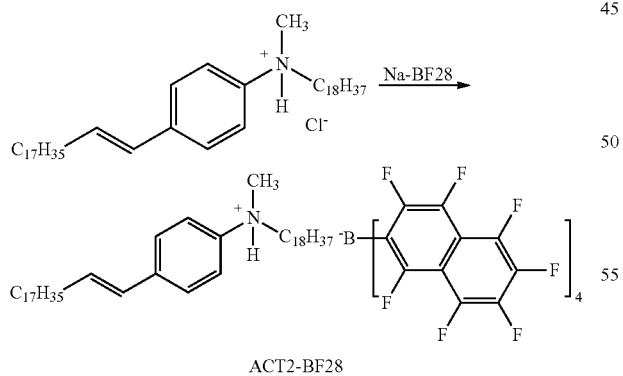

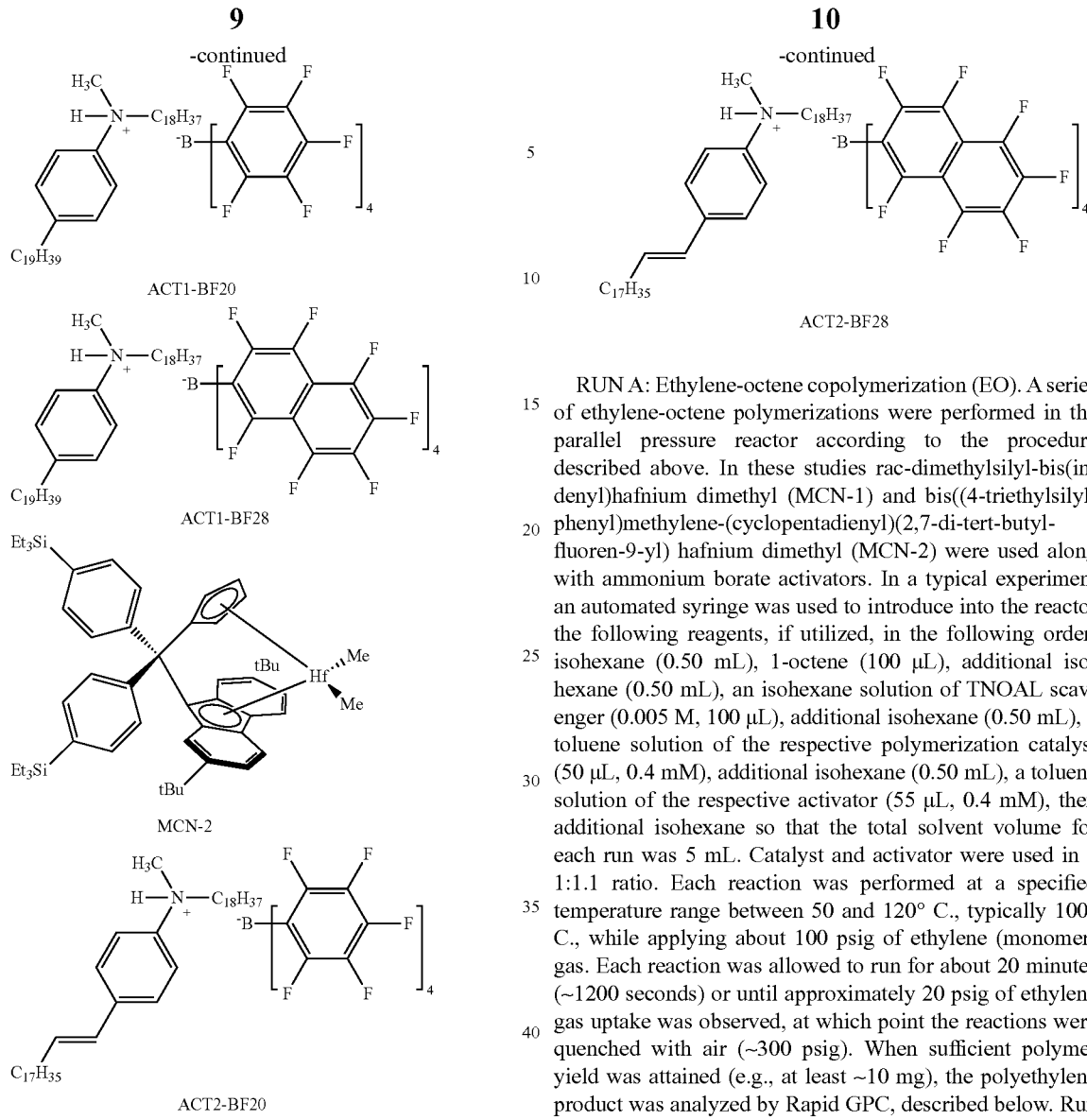

RUN A: Ethylene-octene copolymerization (EO). A series of ethylene-octene polymerizations were performed in the parallel pressure reactor according to the procedure described above. In these studies rac-dimethylsilyl-bis(indenyl)hafnium dimethyl (MCN-1) and bis((4-triethylsilyl) phenyl)methylene-(cyclopentadienyl)(2,7-di-tert-butyl-fluoren-9-yl) hafnium dimethyl (MCN-2) were used along with ammonium borate activators. In a typical experiment an automated syringe was used to introduce into the reactor the following reagents, if utilized, in the following order: isohexane (0.50 mL), 1-octene (100 µL), additional isohexane (0.50 mL), an isohexane solution of TNOAL scavenger (0.005 M, 100 µL), additional isohexane (0.50 mL), a toluene solution of the respective polymerization catalyst (50 µL, 0.4 mM), additional isohexane (0.50 mL), a toluene solution of the respective activator (55 µL, 0.4 mM), then additional isohexane so that the total solvent volume for each run was 5 mL. Catalyst and activator were used in a 1:1.1 ratio. Each reaction was performed at a specified temperature range between 50 and 120° C., typically 100° C., while applying about 100 psig of ethylene (monomer) gas. Each reaction was allowed to run for about 20 minutes (~1200 seconds) or until approximately 20 psig of ethylene gas uptake was observed, at which point the reactions were quenched with air (~300 psig). When sufficient polymer yield was attained (e.g., at least ~10 mg), the polyethylene product was analyzed by Rapid GPC, described below. Run conditions and data are reported in Table 1.

TABLE 1

Data for the ethylene-octene copolymerization.

| Entry | Activator | Catalyst | time (s) | yield (g) | activity (kg/mmol/h) | $M_w$ | $M_n$ | PDI | octene incorporation (wt %) | $T_m$ (° C.) |
|---|---|---|---|---|---|---|---|---|---|---|
| 1 | DMAH-BF20 | MCN-1 | 39.0 | 0.087 | 401.5 | 243,164 | 141,188 | 1.7 | 30.0 | 42.3 |
| 2 | DMAH-BF20 | MCN-1 | 41.8 | 0.082 | 353.1 | 287,394 | 151,452 | 1.9 | 29.7 | 43.3 |
| 3 | DMAH-BF20 | MCN-1 | 35.3 | 0.084 | 428.3 | 253,410 | 140,833 | 1.8 | 29.3 | 45.4 |
| 4 | DMAH-BF20 | MCN-1 | 44.6 | 0.077 | 310.8 | 246,349 | 150,963 | 1.6 | 26.4 | 44.4 |
| 5 | DMAH-BF28 | MCN-1 | 70.4 | 0.090 | 230.1 | 496,965 | 298,315 | 1.7 | 28.2 | 45.7 |
| 6 | DMAH-BF28 | MCN-1 | 64.8 | 0.084 | 233.3 | 494,135 | 301,457 | 1.6 | 28.9 | 47.2 |
| 7 | DMAH-BF28 | MCN-1 | 44.0 | 0.089 | 364.1 | 498,272 | 294,362 | 1.7 | 25.9 | 67.7 |
| 8 | DMAH-BF28 | MCN-1 | 39.9 | 0.080 | 360.9 | 458,206 | 279,729 | 1.6 | 29.8 | 47.7 |
| 9 | ACT1-BF20 | MCN-1 | 51.4 | 0.088 | 308.2 | 281,905 | 149,258 | 1.9 | 30.4 | 42.1 |
| 10 | ACT1-BF20 | MCN-1 | 55.9 | 0.082 | 264.0 | 337,143 | 202,964 | 1.7 | 28.2 | 45.5 |
| 11 | ACT1-BF20 | MCN-1 | 41.6 | 0.077 | 333.2 | 267,895 | 141,356 | 1.9 | 28.9 | 44.8 |
| 12 | ACT1-BF20 | MCN-1 | 40.3 | 0.082 | 366.3 | 281,610 | 159,222 | 1.8 | 32.6 | 46.4 |
| 13 | ACT1-BF28 | MCN-1 | 50.1 | 0.088 | 316.2 | 426,897 | 212,627 | 2.0 | 29.4 | 43.8 |
| 14 | ACT1-BF28 | MCN-1 | 46.8 | 0.082 | 315.4 | 414,062 | 228,305 | 1.8 | 33.0 | 45.0 |
| 15 | ACT1-BF28 | MCN-1 | 59.0 | 0.074 | 225.8 | 563,012 | 312,306 | 1.8 | 28.0 | 49.7 |
| 16 | ACT1-BF28 | MCN-1 | 72.8 | 0.064 | 158.2 | 573,160 | 340,793 | 1.7 | 23.6 | 66.7 |
| 17 | ACT2-BF20 | MCN-1 | 28.1 | 0.082 | 525.3 | 234,775 | 122,764 | 1.9 | 29.9 | 41.9 |
| 18 | ACT2-BF20 | MCN-1 | 43.4 | 0.076 | 315.2 | 348,521 | 194,092 | 1.8 | 25.4 | 66.8 |

TABLE 1-continued

Data for the ethylene-octene copolymerization.

| Entry | Activator | Catalyst | time (s) | yield (g) | activity (kg/mmol/h) | $M_w$ | $M_n$ | PDI | octene incorporation (wt %) | $T_m$ (° C.) |
|---|---|---|---|---|---|---|---|---|---|---|
| 19 | ACT2-BF20 | MCN-1 | 53.4 | 0.066 | 222.5 | 372,511 | 220,367 | 1.7 | 28.6 | 48.9 |
| 20 | ACT2-BF28 | MCN-1 | 68.4 | 0.085 | 223.7 | 511,365 | 294,217 | 1.7 | 28.1 | 45.5 |
| 21 | ACT2-BF28 | MCN-1 | 56.8 | 0.075 | 237.7 | 513,450 | 292,269 | 1.8 | 26.9 | 48.4 |
| 22 | ACT2-BF28 | MCN-1 | 504.2 | 0.050 | 17.9 | 782,626 | 499,302 | 1.6 | 23.8 | 70.7 |
| 23 | DMAH-BF20 | MCN-2 | 95.4 | 0.078 | 147.2 | 989,122 | 531,800 | 1.9 | 33.3 | 45.0 |
| 24 | DMAH-BF20 | MCN-2 | 112.8 | 0.087 | 138.8 | 945,498 | 544,988 | 1.7 | 31.7 | 46.5 |
| 25 | DMAH-BF20 | MCN-2 | 66.5 | 0.075 | 203.0 | 797,796 | 357,723 | 2.2 | 36.5 | 44.5 |
| 26 | DMAH-BF20 | MCN-2 | 62.8 | 0.088 | 252.2 | 849,859 | 461,230 | 1.8 | 33.3 | 48.9 |
| 27 | DMAH-BF28 | MCN-2 | 170.4 | 0.081 | 85.6 | 1,137,824 | 646,823 | 1.8 | 32.0 | 49.6 |
| 28 | DMAH-BF28 | MCN-2 | 108.0 | 0.082 | 136.7 | 1,429,880 | 813,382 | 1.8 | 28.4 | 60.9 |
| 29 | DMAH-BF28 | MCN-2 | 70.1 | 0.085 | 218.3 | 1,231,033 | 658,419 | 1.9 | 29.4 | 50.4 |
| 30 | DMAH-BF28 | MCN-2 | 71.8 | 0.083 | 208.1 | 1,436,846 | 764,922 | 1.9 | 24.0 | 68.8 |
| 31 | ACT1-BF20 | MCN-2 | 98.0 | 0.088 | 161.6 | 786,335 | 453,136 | 1.7 | 35.5 | 43.1 |
| 32 | ACT1-BF20 | MCN-2 | 97.2 | 0.095 | 175.9 | 954,751 | 494,594 | 1.9 | 35.3 | 44.7 |
| 33 | ACT1-BF20 | MCN-2 | 73.7 | 0.097 | 236.9 | 899,437 | 414,978 | 2.2 | 34.1 | 48.6 |
| 34 | ACT1-BF20 | MCN-2 | 70.0 | 0.072 | 185.1 | 862,091 | 445,533 | 1.9 | 32.6 | 47.9 |
| 35 | ACT1-BF28 | MCN-2 | 118.2 | 0.077 | 117.3 | 950,272 | 482,936 | 2.0 | 37.8 | 42.8 |
| 36 | ACT1-BF28 | MCN-2 | 77.1 | 0.065 | 151.8 | 1,102,061 | 586,735 | 1.9 | 32.7 | 43.3 |
| 37 | ACT1-BF28 | MCN-2 | 90.1 | 0.077 | 153.8 | 1,417,429 | 703,024 | 2.0 | 28.1 | 65.3 |
| 38 | ACT1-BF28 | MCN-2 | 94.8 | 0.066 | 125.3 | 1,784,474 | 945,874 | 1.9 | 23.3 | 74.1 |
| 39 | ACT2-BF20 | MCN-2 | 81.6 | 0.097 | 214.0 | 786,176 | 326,583 | 2.4 | 39.2 | 43.3 |
| 40 | ACT2-BF20 | MCN-2 | 68.8 | 0.094 | 245.9 | 815,360 | 364,255 | 2.2 | 34.4 | 42.3 |
| 41 | ACT2-BF20 | MCN-2 | 109.3 | 0.072 | 118.6 | 1,391,637 | 791,773 | 1.8 | 29.1 | 66.0 |
| 42 | ACT2-BF20 | MCN-2 | 106.2 | 0.070 | 118.6 | 1,472,270 | 864,494 | 1.7 | 27.2 | 67.0 |
| 43 | ACT2-BF28 | MCN-2 | 154.5 | 0.084 | 97.9 | 1,387,255 | 693,291 | 2.0 | 29.1 | 45.5 |
| 44 | ACT2-BF28 | MCN-2 | 124.5 | 0.086 | 124.3 | 1,582,669 | 809,661 | 2.0 | 29.1 | 48.2 |
| 45 | ACT2-BF28 | MCN-2 | 251.6 | 0.054 | 38.6 | 2,170,663 | 1,256,775 | 1.7 | 27.9 | 65.5 |

Figure 2:
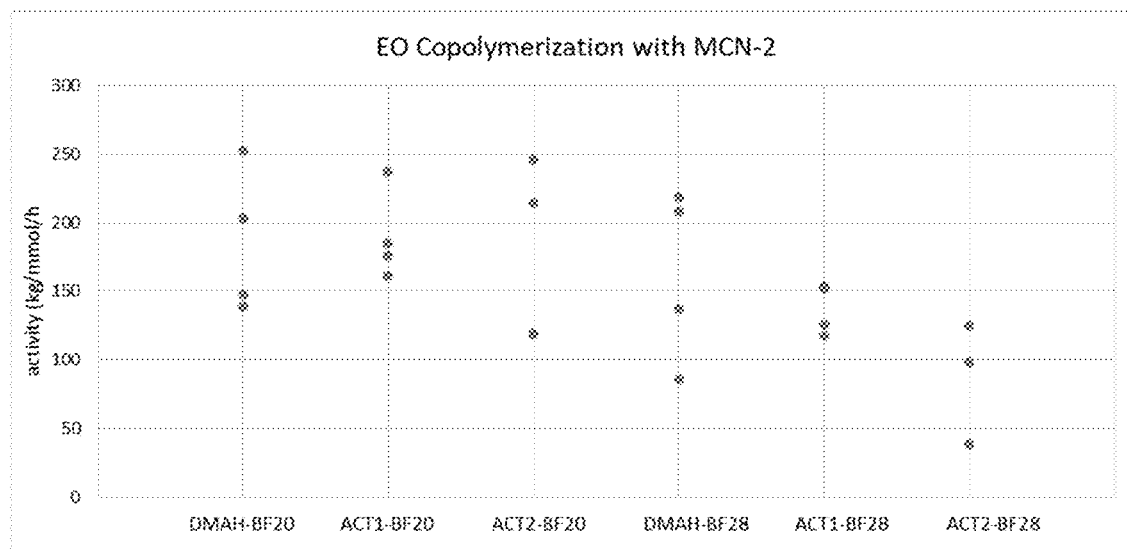
FIG. 2 is a graph illustrating activity using activators embodying the present technological advancement in an ethelyne-octene (EO) copolymerization process.

General conditions: catalyst = 20 nmol;
activator = 22 nmol;
1-octene = 100 µL;
solvent = isohexane;
volume = 5 mL;
tri(n-octyl)aluminum = 500 nmol;
T = 100° C.;
P = 100 PSI The data in Table 1 is depicted in FIGS. 1 and 2.

RUN B: Propylene homopolymerization (PP). The parallel pressure reactor was prepared as described above and purged with propylene. In these polymerizations, the metallocene rac-dimethylsilyl-bis(indenyl)hafnium dimethyl (MCN-1) and bis((4-triethylsilyl)phenyl)methylene-(cyclopentadienyl)(2,7-di-tert-butyl-fluoren-9-yl) hafnium dimethyl (MCN-2) was used along with several different ammonium borate activators. The activators were prepared in solutions of toluene. Isohexane was then injected into each vessel at room temperature followed by a predetermined amount of propylene gas. The reactor was heated to the set temperature while stirring at 800 rpm, and the scavenger, activator and catalyst solutions were injected sequentially to each vessel. The polymerization was allowed to proceed as described previously. Each reaction was allowed to run for about 20 minutes (~1200 seconds) or until approximately 4 psig of propylene gas uptake was observed. Run conditions and data are reported in Table 2.

TABLE 2

Data for the propylene homopolymerization

| entry | activator | catalyst | time (s) | yield (g) | activity (kg/mmol/h) | Mw | Mn | PDI | $T_m$ (° C.) |
|---|---|---|---|---|---|---|---|---|---|
| 1 | DMAH-BF20 | MCN-1 | 92.6 | 0.052 | 101.1 | 33,314 | 21,325 | 1.6 | 116.3 |
| 2 | DMAH-BF20 | MCN-1 | 87.4 | 0.069 | 142.1 | 34,864 | 20,874 | 1.7 | 117.7 |
| 3 | DMAH-BF20 | MCN-1 | 84.8 | 0.084 | 178.3 | 31,253 | 19,801 | 1.6 | 120.7 |
| 4 | DMAH-BF20 | MCN-1 | 80.0 | 0.087 | 195.8 | 33,732 | 21,696 | 1.6 | 121.0 |
| 5 | DMAH-BF28 | MCN-1 | 92.7 | 0.056 | 108.7 | 81,125 | 53,040 | 1.5 | 127.6 |
| 6 | DMAH-BF28 | MCN-1 | 96.3 | 0.081 | 151.4 | 83,338 | 52,135 | 1.6 | 127.5 |
| 7 | DMAH-BF28 | MCN-1 | 171.2 | 0.059 | 62.0 | 89,602 | 57,466 | 1.6 | 127.9 |
| 8 | DMAH-BF28 | MCN-1 | 95.3 | 0.080 | 151.1 | 79,405 | 49,076 | 1.6 | 126.6 |
| 9 | ACT1-BF20 | MCN-1 | 79.5 | 0.094 | 212.8 | 34,035 | 21,918 | 1.6 | 114.4 |
| 10 | ACT1-BF20 | MCN-1 | 96.7 | 0.081 | 150.8 | 34,573 | 22,752 | 1.5 | 116.9 |
| 11 | ACT1-BF20 | MCN-1 | 132.8 | 0.056 | 75.9 | 34,375 | 22,512 | 1.5 | 121.0 |
| 12 | ACT1-BF20 | MCN-1 | 410.6 | 0.040 | 17.5 | 40,444 | 28,590 | 1.4 | 122.0 |
| 13 | ACT1-BF28 | MCN-1 | 79.3 | 0.073 | 165.7 | 72,876 | 50,732 | 1.4 | 128.1 |
| 14 | ACT1-BF28 | MCN-1 | 76.0 | 0.085 | 201.3 | 75,817 | 51,871 | 1.5 | 126.0 |
| 15 | ACT1-BF28 | MCN-1 | 82.4 | 0.063 | 137.6 | 71,856 | 46,435 | 1.5 | 125.6 |
| 16 | ACT1-BF28 | MCN-1 | 81.0 | 0.070 | 155.6 | 66,706 | 42,539 | 1.6 | 119.0 |

TABLE 2-continued

Data for the propylene homopolymerization

| entry | activator | catalyst | time (s) | yield (g) | activity (kg/mmol/h) | Mw | Mn | PDI | $T_m$ (° C.) |
|---|---|---|---|---|---|---|---|---|---|
| 17 | ACT2-BF20 | MCN-1 | 69.0 | 0.153 | 399.1 | 52,204 | 32,869 | 1.6 | 127.3 |
| 18 | ACT2-BF20 | MCN-1 | 67.1 | 0.094 | 252.2 | 32,882 | 20,510 | 1.6 | 115.9 |
| 19 | ACT2-BF20 | MCN-1 | 117.3 | 0.072 | 110.5 | 39,740 | 25,945 | 1.5 | 122.6 |
| 20 | ACT2-BF20 | MCN-1 | 73.9 | 0.104 | 253.3 | 31,920 | 19,828 | 1.6 | 120.3 |
| 21 | ACT2-BF28 | MCN-1 | 95.2 | 0.084 | 158.8 | 204,874 | 129,700 | 1.6 | 128.3 |
| 22 | ACT2-BF28 | MCN-1 | 123.4 | 0.059 | 86.1 | 81,921 | 54,777 | 1.5 | 127.0 |
| 23 | ACT2-BF28 | MCN-1 | 124.8 | 0.060 | 86.5 | 83,983 | 53,108 | 1.6 | 125.1 |
| 24 | ACT2-BF28 | MCN-1 | 147.6 | 0.057 | 69.5 | 83,160 | 52,236 | 1.6 | 125.9 |
| 25 | DMAH-BF20 | MCN-2 | 885.2 | 0.028 | 5.7 | 194,241 | 127,462 | 1.5 | |
| 26 | DMAH-BF20 | MCN-2 | 812.8 | 0.024 | 5.3 | 179,657 | 118,981 | 1.5 | |
| 27 | DMAH-BF20 | MCN-2 | 1201 | 0.022 | 3.3 | 202,965 | 127,142 | 1.6 | |
| 28 | DMAH-BF20 | MCN-2 | 643.7 | 0.024 | 6.7 | 214,548 | 140,242 | 1.5 | |
| 29 | DMAH-BF28 | MCN-2 | 900.0 | 0.030 | 6.0 | 267,242 | 159,461 | 1.7 | |
| 30 | DMAH-BF28 | MCN-2 | 861.9 | 0.029 | 6.1 | 243,828 | 158,368 | 1.5 | |
| 31 | DMAH-BF28 | MCN-2 | 1004 | 0.023 | 4.1 | 264,637 | 176,518 | 1.5 | |
| 32 | DMAH-BF28 | MCN-2 | 1200 | 0.016 | 2.4 | 557,681 | 365,977 | 1.5 | |
| 33 | ACT1-BF20 | MCN-2 | 731.5 | 0.029 | 7.1 | 213,451 | 132,008 | 1.6 | |
| 34 | ACT1-BF20 | MCN-2 | 822.7 | 0.031 | 6.8 | 157,066 | 106,951 | 1.5 | |
| 35 | ACT1-BF20 | MCN-2 | 1201 | 0.008 | 1.2 | | | | |
| 36 | ACT1-BF20 | MCN-2 | 1200 | 0.001 | 0.1 | | | | |
| 37 | ACT1-BF28 | MCN-2 | 652.4 | 0.031 | 8.6 | 246,105 | 154,272 | 1.6 | |
| 38 | ACT1-BF28 | MCN-2 | 700.9 | 0.031 | 8.0 | 256,710 | 176,164 | 1.5 | |
| 39 | ACT1-BF28 | MCN-2 | 1201 | 0.016 | 2.4 | 206,433 | 128,390 | 1.6 | |
| 40 | ACT1-BF28 | MCN-2 | 1201 | 0.009 | 1.3 | | | | |

Figure 3:
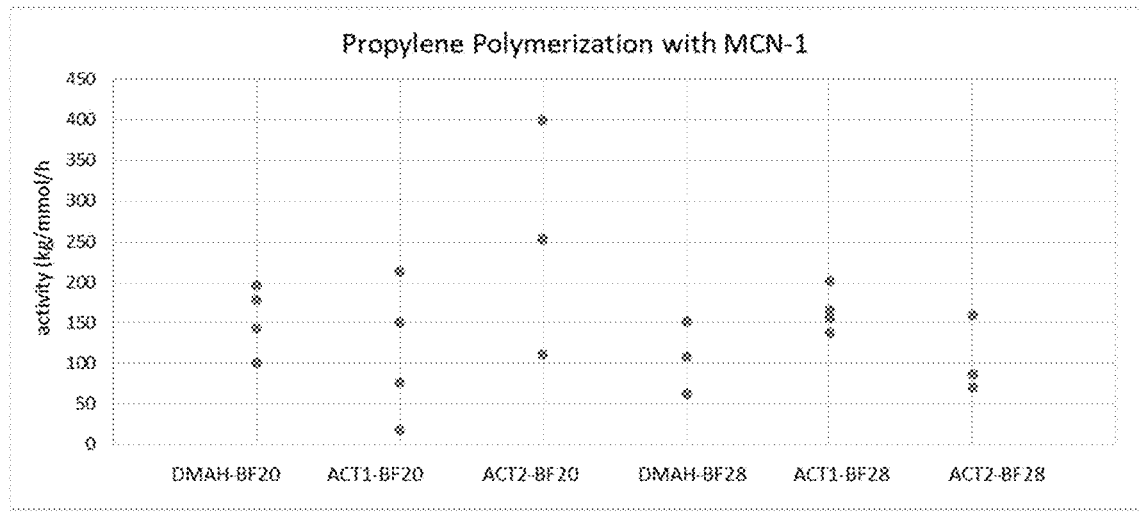
FIG. 3 is a graph illustrating activity using activators embodying the present technological advancement in a propelne polymerization process.

General conditions: catalyst = 20 nmol;
activator = 22 nmol;
solvent = isohexane;
volume = 5 mL;
tri(n-octyl)aluminum = 500 nmol;
T = 100° C.;
P = 160 PSI The data in Table 2 for MCN-1 is depicted in FIG. 3.

When an activator of the present disclosure is used with a catalyst compound (such as a group 4 metallocene compound) in an olefin polymerization, a polymer can be formed having a higher molecular weight and melt temperature than polymers formed using comparative activators.

The present disclosure relates to a catalyst system comprising a transition metal compound and an activator compound as described herein, to the use of such activator compounds for activating a transition metal compound in a catalyst system for polymerizing olefins, and to processes for polymerizing olefins, the process comprising contacting under polymerization conditions one or more olefins with a catalyst system comprising a transition metal compound and such activator compounds.

Catalyst systems of the present disclosure may be formed by combining the catalysts with activators in any suitable manner, including by supporting them for use in slurry or gas phase polymerization. The catalyst systems may also be added to or generated in solution polymerization or bulk polymerization (in the monomer, i.e., little or no solvent).

The typical activator-to-catalyst ratio is about a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

In embodiments herein, the catalyst system may comprise a support material. In at least one embodiment, the support material is a porous support material, for example, talc, or inorganic oxides. Other support materials include zeolites, clays, organoclays, or any other suitable organic or inorganic support material and the like, or mixtures thereof.

In at least one embodiment, the support material is an inorganic oxide. Suitable inorganic oxide materials for use in catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be used, for example, functionalized polyolefins, such as polypropylene. Supports include magnesia, titania, zirconia, montmorillonite, phyllosilicate, zeolites, talc, clays, and the like. Also, combinations of these support materials may be used, for example, silica-chromium, silica-alumina, silica-titania, and the like. Support materials include $Al_2O_3$, $ZrO_2$, $SiO_2$, $SiO_2/Al_2O_3$, $SiO_2/TiO_2$, silica clay, silicon oxide/clay, or mixtures thereof.

Exemplary silicas are marketed under the tradenames of DAVISON 952 or DAVISON 955 by the Davison Chemical Division of W.R. Grace and Company. In other embodiments DAVISON 948 can be used.

In embodiments herein, the present disclosure provides polymerization processes where monomer (such as propylene or ethylene), and optionally comonomer, are contacted with a catalyst system comprising an activator and at least one catalyst compound, as described above. The catalyst compound and activator may be combined in any order, and are combined typically prior to contacting with the monomer.

In at least one embodiment, a polymerization process includes a) contacting one or more olefin monomers with a catalyst system comprising: i) an activator and ii) a catalyst compound of the present disclosure. The activator is a non-coordination anion activator. The one or more olefin monomers may be propylene and/or ethylene and the polymerization process further comprises heating the one or more olefin monomers and the catalyst system to 70° C. or more to form propylene polymers or ethylene polymers, such as propylene polymers.

Polymerization processes of the present disclosure can be carried out in any suitable manner. Any suitable suspension, homogeneous, bulk, solution, slurry, or gas phase polymerization process can be used. Such processes can be run in a batch, semi-batch, or continuous mode. Homogeneous polymerization processes and slurry processes can be performed. (A useful homogeneous polymerization process is one where at least 90 wt % of the product is soluble in the reaction media.) A bulk homogeneous process can be used. (An example bulk process is one where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In at least one embodiment, the process is a slurry polymerization process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Polymerizations can be performed at any temperature and/or pressure suitable to obtain the desired polymers, such as ethylene and or propylene polymers. Typical temperatures and/or pressures include a temperature in the range of from 0° C. to 300° C., such as 20° C. to 200° C., such as 35° C. to 150° C., such as 40° C. to 120° C., such as 45° C. to 80° C., for example about 74° C., and at a pressure in the range of from 0.35 MPa to 10 MPa, such as 0.45 MPa to 6 MPa, such as 0.5 MPa to 4 MPa.

In a typical polymerization, the run time of the reaction is up to 300 minutes, such as in the range of from 30 seconds to 250 minutes, such as 10 to 120 minutes.

Other additives may also be used in the polymerization, as desired, such as one or more scavengers, promoters, modifiers, chain transfer agents (such as diethyl zinc), hydrogen, or aluminum alkyls. Useful chain transfer agents are typically alkylalumoxanes, a compound represented by the formula $AlR_3$, $ZnR_2$ (where each R is, independently, a $C_1$-$C_8$ aliphatic radical, such as methyl, ethyl, propyl, butyl, phenyl, hexyl, octyl or an isomer thereof) or a combination thereof, such as diethyl zinc, methylalumoxane, trimethylaluminum, triisobutylaluminum, trioctylaluminum, or a combination thereof.

The present disclosure also provides compositions of matter which can be produced by the methods described herein.

In at least one embodiment, a polyolefin is a propylene homopolymer, an ethylene homopolymer or an ethylene copolymer, such as propylene-ethylene and/or ethylene-alphaolefin (such as $C_4$ to $C_{20}$) copolymer (such as an ethylene-hexene copolymer or an ethylene-octene copolymer). A polyolefin can have an Mw/Mn of greater than 1 to 4 (such as greater than 1 to 3).

In at least one embodiment, a polyolefin is a homopolymer of ethylene or propylene or a copolymer of ethylene such as a copolymer of ethylene having from 0.1 to 25 wt % (such as from 0.5 to 20 wt %, such as from 1 to 15 wt %, such as from 5 to 17 wt %) of ethylene with the remainder balance being one or more $C_3$ to $C_{20}$ olefin comonomers (such as $C_3$ to $C_{12}$ alpha-olefin, such as propylene, butene, hexene, octene, decene, dodecene, such as propylene, butene, hexene, octene). A polyolefin can be a copolymer of propylene such as a copolymer of propylene having from 0.1 to 25 wt % (such as from 0.5 to 20 wt %, such as from 1 to 15 wt %, such as from 3 to 10 wt %) of propylene and from 99.9 to 75 wt % of one or more of $C_2$ or $C_4$ to $C_{20}$ olefin comonomer (such as ethylene or $C_4$ to $C_{12}$ alpha-olefin, such as butene, hexene, octene, decene, dodecene, such as ethylene, butene, hexene, octene).

In at least one embodiment, a polyolefin, such as a polypropylene (e.g., iPP) or an ethylene-octene copolymer, has an Mw from 30,000 to 205,000, such as from 50,000 to 100,000, such as from 70,000 to 85,000.

In at least one embodiment, a polyolefin, such as a polypropylene (e.g., iPP) or an ethylene-octene copolymer, has an Mn from 100,000 to 1,300,000, such as from 200,000 to 1,000,000, such as from 300,000 to 900,000, such as from 400,000 to 700,000.

In at least one embodiment, a polyolefin, such as a polypropylene (e.g., iPP) or an ethylene-octene copolymer, has a melt temperature (Tm) of from 40° C. to 80° C., such as 50° C. to 70° C.

In at least one embodiment, the polymer is an ethylene copolymer, and the comonomer is octene, at a comonomer content of from 20 wt % to 40 wt % octene, such as from 25 wt % to 35 wt %.

In another embodiment, the polymer (such as the polyethylene or polypropylene) produced herein is combined with one or more additional polymers prior to being formed into a film, molded part or other article.

One or more of the foregoing polymers, such as the foregoing polyethylenes, polypropylenes, or blends thereof, may be used in a variety of end-use applications. Such applications include, for example, mono- or multi-layer blown, extruded, and/or shrink films.

Overall, activators, catalyst systems, and methods of the present disclosure can provide improved solubility in aliphatic solvents, as compared to conventional activator compounds and catalyst systems. Activators, catalyst systems, and methods of the present disclosure can provide polyolefins having a weight average molecular weight (Mw) of about 100,000 g/mol or greater and a melt temperature (Tm) of about 110° C. or greater.

The distribution and the moments of molecular weight (Mw, Mn, Mw/Mn, etc.), the comonomer content and the long chain branching (g') are determined by using a high temperature Gel Permeation Chromatography (Polymer Char GPC-IR) equipped with a multiple-channel band-filter based Infrared detector IR5, an 18-angle light scattering detector and a viscometer. Three Agilent PLgel 10 μm Mixed-B LS columns are used to provide polymer separation. Aldrich reagent grade 1,2,4-trichlorobenzene (TCB) with 300 ppm antioxidant butylated hydroxytoluene (BHT) is used as the mobile phase. The TCB mixture is filtered through a 0.1 μm Teflon filter and degassed with an online degasser before entering the GPC instrument. The nominal flow rate is 1.0 mL/min and the nominal injection volume is 200 μL. The whole system including transfer lines, columns, detectors are contained in an oven maintained at 145° C. Given amount of polymer sample is weighed and sealed in a standard vial with 80 μL flow marker (Heptane) added to it. After loading the vial in the autosampler, polymer is automatically dissolved in the instrument with 8 mL added TCB solvent. The polymer is dissolved at 160° C. with continuous shaking for about 1 hour for most PE samples or 2 hour for PP samples. The TCB densities used in concentration calculation are 1.463 g/ml at room temperature and 1.284 g/ml at 145° C. The sample solution concentration is from 0.2 to 2.0 mg/ml, with lower concentrations being used for higher molecular weight samples.

The concentration (c), at each point in the chromatogram is calculated from the baseline-subtracted IR5 broadband signal intensity (I), using the following equation:

$$c = \beta I$$

where β is the mass constant determined with PE or PP standards. The mass recovery is calculated from the ratio of the integrated area of the concentration chromatography over elution volume and the injection mass which is equal to the pre-determined concentration multiplied by injection loop volume.

The conventional molecular weight (IR MW) is determined by combining universal calibration relationship with the column calibration which is performed with a series of monodispersed polystyrene (PS) standards ranging from 700 to 10M. The MW at each elution volume is calculated with following equation;

$$\log M = \frac{\log(K_{PS}/K)}{a+1} + \frac{a_{PS}+1}{a+1} \log M_{PS}$$

where the variables with subscript "PS" stands for polystyrene while those without a subscript are for the test samples. In this method, $a_{PS}=0.67$ and $K_{PS}=0.000175$ while a and K are calculated as described in the published in literature (Sun, T. et al. (2001) "Effect of Short Chain Branching on the Coil Dimensions of Polyolefins in Dilute Solutions," *Macromolecules*, v. 34(19), pp. 6812-6820), except that for purposes of this invention and claims thereto, $\alpha=0.695$ and $K=0.000579$ for linear ethylene polymers, $\alpha=0.705$ and $K=0.0002288$ for linear propylene polymers, $\alpha=0.695+(0.01*(wt.\ fraction\ propylene))$ and $K=0.000579-(0.0003502*(wt.\ fraction\ propylene))$ for ethylene-propylene copolymers. Concentrations are expressed in g/cm³, molecular weight is expressed in g/mole, and intrinsic viscosity (hence K in the Mark-Houwink equation) is expressed in dL/g unless otherwise noted.

The comonomer composition is determined by the ratio of the IR5 detector intensity corresponding to $CH_2$ and $CH_3$ channel calibrated with a series of PE and PP homo/copolymer standards whose nominal value are predetermined by NMR or FTIR such as EMCC commercial grades about LLDPE, Vistamaxx, ICP, etc.

Melting Temperature, Tm, is measured by differential scanning calorimetry ("DSC") using a DSCQ200 unit. The sample is first equilibrated at 25° C. and subsequently heated to 220° C. using a heating rate of 10° C./min (first heat). The sample is held at 220° C. for 3 minutes. The sample is subsequently cooled down to −100° C. with a constant cooling rate of 10° C./min (first cool). The sample is equilibrated at −100° C. before being heated to 220° C. at a constant heating rate of 10° C./min (second heat). The exothermic peak of crystallization (first cool) is analyzed using the TA Universal Analysis software and the corresponding to 10° C./min cooling rate is determined. The endothermic peak of melting (second heat) is also analyzed using the TA Universal Analysis software and the peak melting temperature (Tm) corresponding to 10° C./min heating rate is determined. In the event of conflict between the DSC Procedure-1 and DSC procedure-2, DSC procedure-2 is used.

To determine various molecular weight related values by GPC, high temperature size 5 exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388, each of which is fully incorporated herein by reference for US purposes. This apparatus has a series of three 30 cm×7.5 mm linear columns, each containing PLgel 10 μm, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using an evaporative light scattering detector (as shown by the examples in Table 3) or Polymer Char IR4 detector. The molecular weights presented are relative to linear polystyrene standards and are uncorrected.

Dimer Data

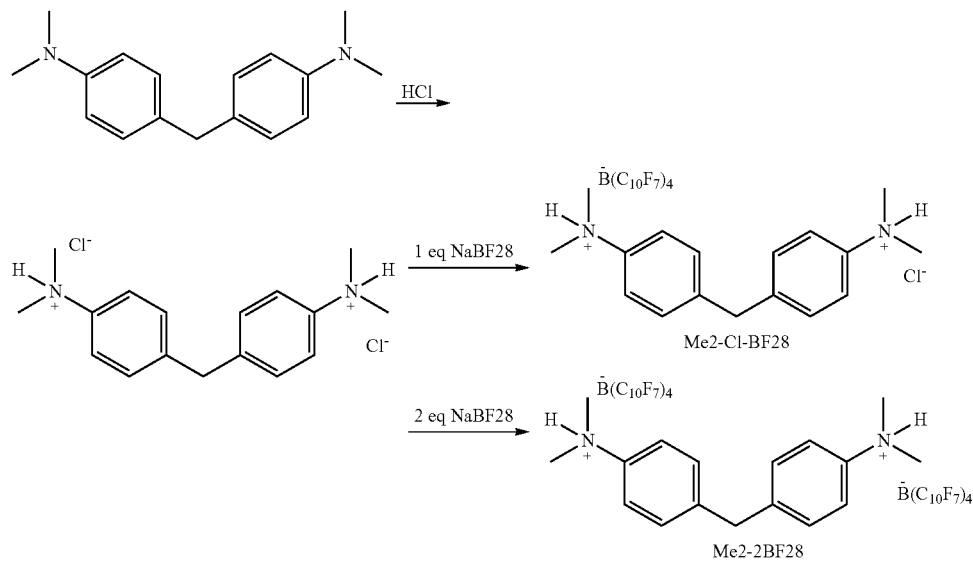

-continued

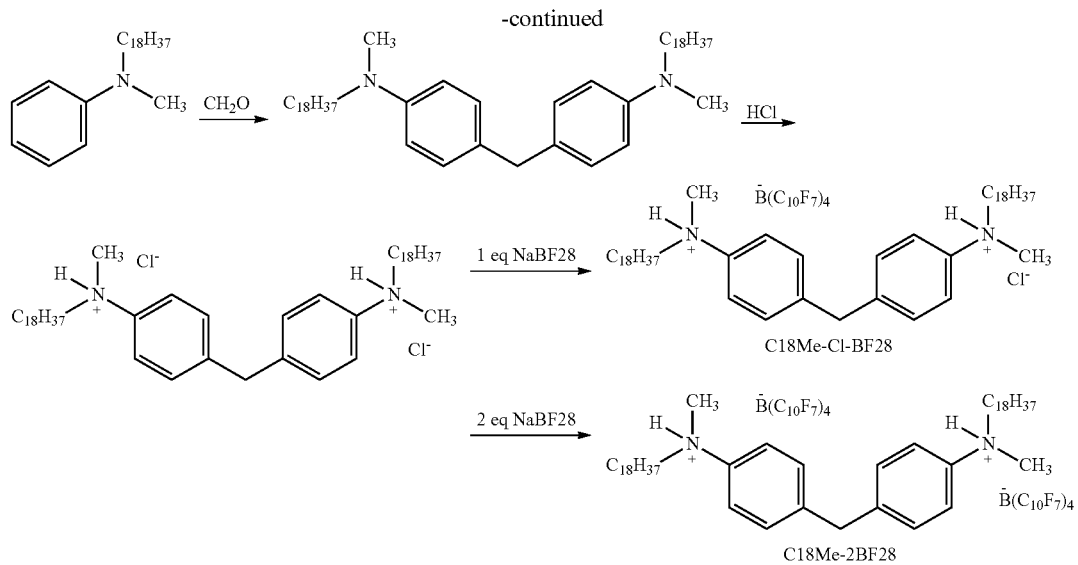

Ethylene-octene copolymerization (EO). A series of ethylene-octene polymerizations were performed in the parallel pressure reactor according to the procedure described above. In these studies rac-dimethylsilyl-bis(indenyl)hafnium dimethyl (MCN-1) was used along with ammonium borate activators. In a typical experiment an automated syringe was used to introduce into the reactor the following reagents, if utilized, in the following order: isohexane (0.50 mL), 1-octene (100 μL), additional isohexane (0.50 mL), an isohexane solution of TNOAL scavenger (0.005 M, 100 μL), additional isohexane (0.50 mL), a toluene solution of the respective polymerization catalyst (50 μL, 0.4 mM), additional isohexane (0.50 mL), a toluene solution of the respective activator (55 μL, 0.4 mM), then additional isohexane so that the total solvent volume for each run was 5 mL. Catalyst and activator were used in a 1:1.1 or 1:0.55 ratio. Each reaction was performed at a specified temperature range between 50 and 120° C., typically 100° C., while applying about 100 psig of ethylene (monomer) gas. Each reaction was allowed to run for about 20 minutes (~1200 seconds) or until approximately 20 psig of ethylene gas uptake was observed, at which point the reactions were quenched with air (~300 psig). When sufficient polymer yield was attained (e.g., at least ~10 mg), the polyethylene product was analyzed by Rapid GPC, described below. Run conditions and data are reported in Table 3.

TABLE 3

Data for ethylene-octene copolymerization

| Entry | Activator | time (s) | yield (g) | activity (kg mmol$^{-1}$ h$^{-1}$) | $M_w$ | $M_n$ | PDI | octene incorp (wt %) | $T_m$ (° C.) |
|---|---|---|---|---|---|---|---|---|---|
| 1 | DMAH-BF28 | 51.4 | 0.086 | 302.4 | 448031 | 224104 | 2.0 | 26.4 | 56.5 |
| 2 | NOMAH-BF28 | 44.6 | 0.085 | 341.6 | 442934 | 213842 | 2.1 | 28.6 | 54.9 |
| 3 | Me2-Cl-BF28 | 1200 | 0.002 | 0.0 | | | | | |
| 4 | Me2-2BF28 | 46.4 | 0.090 | 351.4 | 434350 | 208491 | 2.1 | 29.6 | 53.5 |
| 5 | Me2-2BF28* | 58.9 | 0.078 | 238.7 | 480678 | 238592 | 2.0 | 28.6 | 59.2 |
| 6 | C18Me-Cl-BF28 | 98.9 | 0.062 | 117.7 | 534806 | 281361 | 1.9 | 27.9 | 61.3 |
| 7 | C18Me-2BF28 | 38.9 | 0.095 | 442.0 | 388861 | 173817 | 2.3 | 29.4 | 51.4 |
| 8 | C18Me-2BF28* | 47.3 | 0.086 | 326.5 | 451163 | 219162 | 2.1 | 28.7 | 57.8 |

Figure 4:
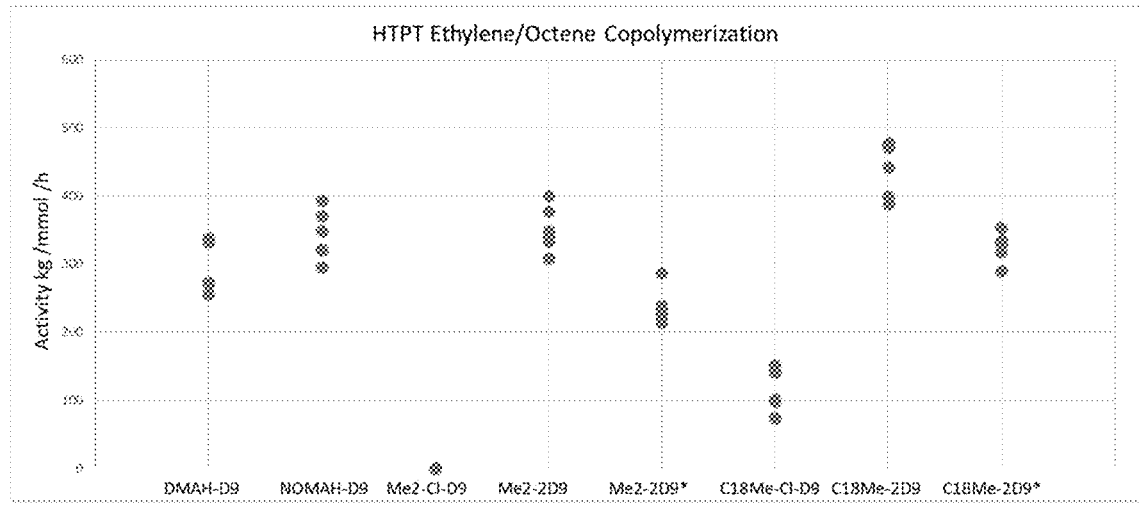
FIG. 4 is a graph illustrating activity vs. activator.

General conditions: MCN-1 catalyst = 20 nmol;
activator = 22 nmol;
*activator = 11 nmol;
1-octene = 100 μL;
solvent = isohexane;
volume = 5 mL;
tri(n-octyl)aluminum = 500 nmol;
T = 100° C.;
P = 100 PSI;
average 6 replicates The data in Table 3 is depicted in FIG. 4.

Propylene homopolymerization (PP). The parallel pressure reactor was prepared as described above and purged with propylene. In these polymerizations, the metallocene rac-dimethylsilyl-bis(indenyl)hafnium dimethyl (MCN-1) was used along with several different ammonium borate activators. The activators were prepared in solutions of toluene. Isohexane was then injected into each vessel at room temperature followed by a predetermined amount of propylene gas. The reactor was heated to the set temperature while stirring at 800 rpm, and the scavenger, activator and catalyst solutions were injected sequentially to each vessel. The polymerization was allowed to proceed as described previously. Each reaction was allowed to run for about 20 minutes (~1200 seconds) or until approximately 4 psig of propylene gas uptake was observed. Run conditions and data are reported in Table 4.

TABLE 4

Data for propylene homopolymerization

| Entry | Activator | time (s) | yield (g) | activity (kg mmol$^{-1}$ h$^{-1}$) | $M_w$ | $M_n$ | PDI | $T_m$ (° C.) |
|---|---|---|---|---|---|---|---|---|
| 1 | DMAH-BF28 | 86.4 | 0.068 | 147.8 | 101428 | 49659 | 2.0 | 125.8 |
| 2 | NOMAH-BF28 | 81.3 | 0.068 | 154.8 | 101961 | 48483 | 2.1 | 125.9 |
| 3 | Me2-Cl-BF28 | 1200.7 | 0.000 | 0.0 | | | | |
| 4 | Me2-2BF28 | 72.3 | 0.105 | 262.6 | 87592 | 41168 | 2.2 | 124.1 |
| 5 | Me2-2BF28* | 131.9 | 0.078 | 106.6 | 104675 | 53576 | 2.0 | 124.7 |
| 6 | C18Me-Cl-BF28 | 1087.8 | 0.035 | 6.6 | 119479 | 60022 | 2.0 | 126.7 |
| 7 | C18Me-2BF28 | 62.8 | 0.107 | 311.9 | 88909 | 42443 | 2.1 | 124.0 |
| 8 | C18Me-2BF28* | 279.3 | 0.091 | 144.0 | 100949 | 49895 | 2.1 | 125.6 |

Figure 5:
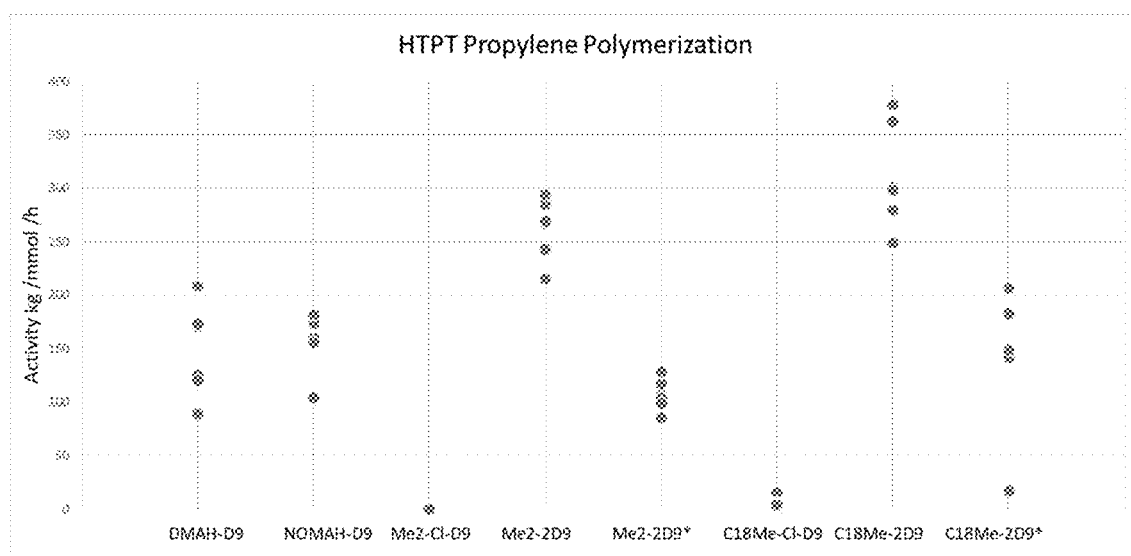
FIG. 5 is a graph illustrating activity vs. activator.

General conditions: MCN-1 catalyst = 20 nmol;
activator = 22 nmol;
*activator = 11 nmol;
1-octene = 100 μL;
solvent = isohexane;
volume = 5 mL;
tri(n-octyl)aluminum = 500 nmol;
T = 100° C.;
P = 160 PSI;
average 5-6 replicates The data in Table 4 is depicted in FIG. 5.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa. The term "about" when used as a modifier for, or in conjunction with, a variable, characteristic or condition is intended to convey that the numbers, ranges, characteristics and conditions disclosed herein are flexible and that practice of the present technological advancement by those skilled in the art using temperatures, rates, times, concentrations, carbon numbers, amounts, contents, properties such as size, density, surface area, etc., that are outside of the stated range or different from a single stated value, will achieve the desired result or results as described in the application, namely, an activated support or catalyst system without detectable toluene. All numerical values within the detailed description herein are modified by "about" or "approximately" the indicated value, and take into account experimental error and variations that would be expected by a person having ordinary skill in the art (unless otherwise noted).

What is claimed is:

1. A composition represented by Formula (AI):

[Ar(ER$^1$R$^2$H)(R$^3$)]$^+$[BR$^4$R$^5$R$^6$R$^7$]$^-$     (AI)

wherein,
Ar is an aromatic group,
E is nitrogen or phosphorous,
R$^1$ is independently selected from aliphatic hydrocarbyl groups containing 1 to 30 carbon atoms,
each of R$^2$ and R$^3$ is independently selected from aliphatic hydrocarbyl groups containing 10 to 30 carbon atoms and at least one internal olefin, and
each of R$^4$, R$^5$, R$^6$, and R$^7$ is independently substituted phenyl or substituted naphthyl, wherein at least one of R$^4$, R$^5$, R$^6$, and R$^7$ is substituted with from one to seven fluorine atoms.

2. The composition of claim 1, wherein R$^1$ is methyl.

3. The composition of claim 1, wherein E is phosphorous.

4. The composition of claim 1, wherein E is nitrogen.

5. The composition of claim 1, wherein each of R$^4$, R$^5$, R$^6$, and R$^7$ is independently substituted phenyl.

6. The composition of claim 1, wherein each of R$^4$, R$^5$, R$^6$, and R$^7$ is independently substituted naphthyl.

7. The composition of claim 1, wherein the olefin is hanging off of R$^3$.

8. A method, comprising:
introducing one or more monomers, an activator, and catalyst into a reactor under polymerization conditions; and
obtaining a polymer,
wherein the activator is a compound represented by Formula (AI):

[Ar(ER$^1$R$^2$H)(R$^3$)][BR$^4$R$^5$R$^6$R$^7$]     (AI)

wherein,
Ar is an aromatic group,
E is nitrogen or phosphorous,
R$^1$ is independently selected from aliphatic hydrocarbyl groups containing 1 to 30 carbon atoms, each of $R^2$ and $R^3$ is independently selected from aliphatic hydrocarbyl groups containing 10 to 30 carbon atoms and at least one internal olefin, and each of $R^4$, $R^5$, $R^6$, and $R^7$ is independently substituted phenyl or substituted naphthyl, wherein at least one of $R^4$, $R^5$, $R^6$, and $R^7$ is substituted with from one to seven fluorine atoms.

9. The method of claim 8, wherein the polymer includes an ethylene copolymer.

10. The method of claim 9, wherein the ethylene copolymer includes an ethylene-octene copolymer.

11. The method of claim 8, wherein the polymer includes propylene.

* * * * *